United States Patent [19]
Chen et al.

[11] Patent Number: 6,100,395
[45] Date of Patent: Aug. 8, 2000

[54] REDUCTIVE ALKYLATION OF SECONDARY AMINES WITH HYDROSILANE

[75] Inventors: Bang-Chi Chen, Plainsboro, N.J.; Joseph E. Sundeen, Yardley, Pa.; Peng Guo, Lawrenceville, N.J.

[73] Assignee: Bristol-Myers Squibb Company, Princeton, N.J.

[21] Appl. No.: 09/480,202

[22] Filed: Jan. 10, 2000

Related U.S. Application Data

[60] Provisional application No. 60/115,587, Jan. 12, 1999.

[51] Int. Cl.$^7$ ............. C07C 209/28; C07D 243/14; C07D 233/64; C07D 333/64
[52] U.S. Cl. ............ 540/504; 546/446; 546/473; 546/397
[58] Field of Search ............ 540/504; 564/397, 564/446, 473

[56] References Cited

FOREIGN PATENT DOCUMENTS

97/30992  8/1997  WIPO .

OTHER PUBLICATIONS

Thomas H. Lowry and Kathleen Schueller Richardson, Mechanism and Theory in Organic Chemistry, 3rd Edition, Harper and Row, New York, 1987, pp. 704 and 708.

E. G. Sander and William P. Jencks, JACS, 90 (22) 1968, 6154–6162.
Dube et al., Tetrahedron Letters, 40, pp. 2295–2298 (1999).
Lockemann, Chemical Abstracts, 25:522 (1931).
Emerson, Org. React., 4, pp. 174–255 (1948).
Schaus et al., Synthetic Communications, 20 , pp. 3553–3562 (1990).
Fujimori et al., Tetrahedron Letters, 21, pp. 3385–3388 (1980).
Verardo et al., Synthetic Communications, 24, pp. 609–627 (1994).
Lee et al., Synthetic Communications, 24, pp. 3129–3134 (1994).
Abdel–Magid et al., J. Org. Chem., 61, pp. 3849–3862 (1996).
Kursanov et al., Synthesis, pp. 633–651 (1974).
Beulshausen et al., Liebigs Ann. Chem., pp. 528–526 (1992).
West et al., J. Org. Chem., 38, pp. 2675–2681 (1973).
Loim et al., Bull. Acad. Sci. USSR, Div. Chem. Sci., p. 1345 (1968).

*Primary Examiner*—Mark L. Berch
*Attorney, Agent, or Firm*—Timothy J. Babcock

[57] ABSTRACT

A novel process for the production of tertiary amines by reductive alkylation of second amine using hydrosilane and a Lewis acid is disclosed. The novel process has applications in the preparation of imidazole-containing benzodiazepines, inhibitors of farnesyl protein transferase.

12 Claims, No Drawings

REDUCTIVE ALKYLATION OF SECONDARY AMINES WITH HYDROSILANE

RELATED APPLICATIONS

This application claims priority benefit under Title 35 § 119(e) of United States Provisional Application No. 60/115,587, filed Jan. 12, 1999, and entitled REDUCTIVE ALKYLATION OF SECONDARY AMINES WITH HYDROSILANE, the entire contents of which are incorporated herein by reference.

BACKGROUND OF THE INVENTION

The present invention concerns a new process for the reductive alkylation of secondary amines using hydrosilane with applications to the preparation of imidazole-containing benzodiazepines, inhibitors of farnesyl protein transferase which find utility in the treatment of a variety of cancers and other diseases (Ding, C. Z.; Hunt, J. T.; Kim, S.-h.; Mitt, T.; Bhide, R.; Leftheris, K. WO 9730992; Chem. Abstr. 1998, 127, 278213).

Many methods have been previously reported for the reductive alkylation of secondary amines with carbonyl compounds in the presence of a reducing agent. The reducing agent includes: zinc (Lockemann, G. DE 503113; Chem. Abstr. 1931, 25, 522), $H_2$/Pd(or Pt, Ni) (Emerson, W. S. Org. React. 1948, 4,174; Schaus, J. M.; Huser, D. L.; Titus, R. D. Synth. Commun. 1990, 20, 3553), selenophenol (Fujimori, K.; Yoshimoto, H.; Oae, S. Tetrahedron Lett. 1980, 21, 3385), $NaBH_4$ (Verardo, G.; Giumanini, A. G.; Strazzolini, P. Synth. Commun. 1994, 24, 609), and $NaCNBH_3$ (Lee, M.; Garbiras, B. J. Synth. Commun. 1994, 24, 3129). All these reducing agents suffer one or more drawbacks. They are either toxic such as selenophenol and $NaCNBH_3$, or are not selective such as zinc, $H_2$)Pd(or Pt, Ni) and $NaBH_4$ since a number of other reducible groups could be affected by these reagents. $NaBH(OAc)_3$ was subsequently introduced to address these problems (Abdel-Magid, A. F.; Carson, K. G.; Harris, B. D.; Maryanoff, C. A.; Shah, R. D. J. Org. Chem. 1996,61, 3849) and this reagent was used in the preparation of the aforementioned imidazole-containing benzodiazepine compounds (Ding, C. Z.; Hunt, J. T.; Kim, S.-h.; Mitt, T.; Bhide, R.; Leftheris, K., WO 9730992; Chem. Abstr. 1998, 127, 278213). Although the desired products were obtained from 1 H-benzodiazepine starting materials, a large excess of aldehyde was required for a satisfactory conversion. In addition, expensive chromatographic separation of products was necessary which rendered this method not amenable to large scale preparation.

Reduction of imines preformed from primary anilines and aldehydes to secondary anilines with $Et_3SiH$/TFA has been previously reported (Kursanov, D. N.; Parnes, Z. N.; Loim, N. M. Synthesis 1974, 633; Loim, N. M. Bull. Acad. Sci. USSR, Div. Chem. Sci. 1968,1345). Reduction of the preformed aminal from secondary amine and formaldehyde to give tertiary amine using $Et_3SiH$/TFA has also been disclosed (Beulshausen, T.; Groth, U.; Schoellkopf, U. Liebigs Ann. Chem. 1992, 523). However, it remains as a question whether the direct reductive alkylation of a secondary amine with an aldehyde using $Et_3SiH$/TFA would work, since it was well documented that aldehydes react readily with $Et_3SiH$/TFA to give the corresponding alcohols and even methylenes (Kursanov, D. N.; Parnes, Z. N.; Loim, N. M. Synthesis 1974, 633; West, C. T.; Donnelly, S. J.; Kooistra, D. A.; Doyle, M. P. J. Org. Chem. 1973, 38, 2675).

SUMMARY OF THE INVENTION

This invention is a new efficient process for the preparation of tertiary amines with applications to the preparation of imidazole-containing benzodiazepines, inhibitors of farnesyl protein transferase. The process involves a new reaction for the reductive alkylation of a secondary amine with an aldehyde using $Et_3SiH$/TFA. Compared with the previously reported synthesis, the new reaction of the present invention is faster, uses lesser amounts of aldehyde and gives a higher yield of the desired product.

DETAILED DESCRIPTION OF THE INVENTION

In its broadest aspect, the present invention provides a more efficient process for the preparation of tertiary amines (IV) from secondary amines (I) and carbonyl compounds (II). The process involves reaction of a secondary amine (I) with a carbonyl compound (II) using a hydrosilane (III) in the presence of a Lewis acid (Scheme 1).

Scheme 1

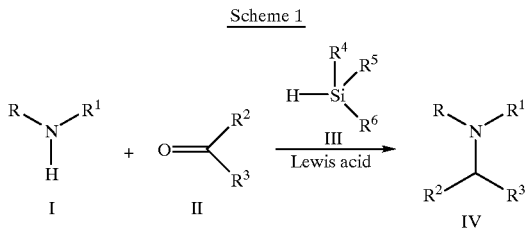

In a more narrow aspect, the invention deals with the preparation of 1-alkyl-2,3,4,5-tetrahydro-1,4-benzodiazepines (VII) from 4-substituted-2,3,4,5-tetrahydro-1,4-benzodiazepines (V) with an aldehyde (VI) using hydrosilane (III) in the presence of Lewis acid (Scheme 2).

Scheme 2

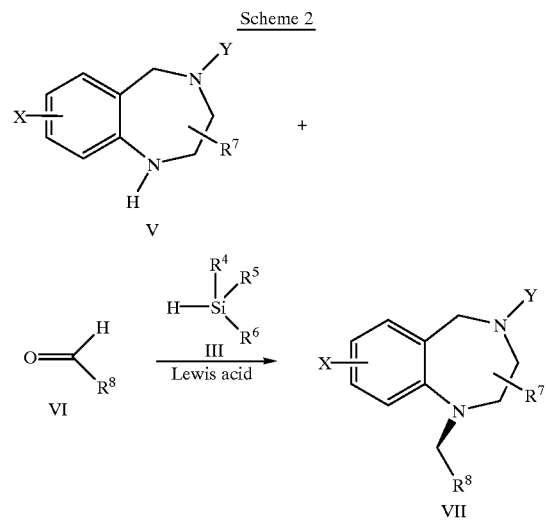

In compounds I, II, III, IV, V, VI and VII, the functional groups R, $R^1$, $R^2$, $R^3$, $R^4$, $R^5$, $R^6$, $R^7$ and $R^8$ can be $C_1$–$C_{12}$ alkyl or $C_1$–$C_{30}$ aryl groups. X can be one or a combination of hydrogen, halogen, R, RO—, RCOO—, ROCOO—, $R^1R^2NCOO$—, $R^1R^2N$—, RS—, $RS(O)_2$—, $ROS(O)_2$—, $R^1,R^2NS(O)_2$—, CN, $NO_2$. Y can be RC(O)—, ROC(O)—, $R_1R_2NC(O)$—, $RS(O)_2$—, $ROS(O)_2$—, $R_1R_2NS(O)_2$—.

Unless otherwise indicated, as used herein the term "alkyl" or derivative forms thereof, refers to straight chain or branched alkyl groups of 1 to 12 carbon atoms, the term "aryl" or derivative forms thereof refers to aryl groups of 1–30 carbon atoms. Examples of alkyl groups include methyl, ethyl, propyl, butyl, isobutyl, pentyl, hexyl and the like. Examples of aryl groups include phenyl, naphthyl, anthryl, biphenyl and the like. The term "halo" refers to Cl, Br, and l.

Lewis acid includes protonic acids and non-protonic acids. Examples of protonic acids include trifluoroacetic acid, trifluoromethanesulfonic acid and the like. Examples of non-protonic acids include boron trifluoride.

As set forth in Scheme 2, the process for the preparation of 1-alkyl-2,3,4,5-tetrahydro-1,4-benzodiazepines involves reaction of a 4-substituted-2,3,4,5-tetrahyrdro-1,4-benzodiazepine with an aldehyde in the presence of a hydrosilane and Lewis acid in a suitable solvent or solvent mixtures.

The 4-substituted-2,3,4,5-tetrahydro-1,4-benzodiazepine includes 4-acyl and 4-sulfonyl-2,3,4,5-tetrahydro-1,4-benzodiazepines with the latter preferred. The aldehyde includes aliphatic and aromatic aldehydes with imidazole4-carboxaldehyde preferred. The hydrosilane used in the reaction includes trialkyl and aryl hydrosilanes with hydrotriethylsilane preferred. The Lewis acid used in the reaction includes protonic acids such as trifluoroacetic acid and trifluoromethanesulfonic acid and non-protonic acids such as boron trifluoride, with trifluoroacetic acid being the preferred Lewis acid. Suitable solvent(s) include hydrocarbons, halogenated hydrocarbons, ethers, esters, amides and nitriles. The preferred solvent is dichloromethane. The reaction temperatures range from −110 to 150° C. with 0–100° C. preferred.

The following examples illustrate the invention but should not be interpreted as a limitation thereon.

EXAMPLE 1

1H-3-(4-fluorobenzyl)-4-(phenylsulfonyl)-7-cyano-2,3,4,5-tetrahydro-1,4-benzodiazepine To a stirred solution of (3R)-3-(4-fluorobenzyl)-7-cyano-2,3,4,5-tetrahydro-1,4-benzodiazepine (3.6 g) in anhydrous methylene chloride (50 mL) and diisopropylethylamine (3.5 mL) was added phenylsulfonyl chloride (1.5 mL) at 0° C. in 20 minutes. The mixture was stirred at room temperature for 5 hours. Methylene chloride (50 mL) and saturated sodium bicarbonate was added and the mixture was stirred for 1 hour. The phases were separated and the organic layer was washed with 1N NaOH (2×20 mL), 10% KHSO4 (2×20 mL) and saturated brine. The solvent was removed to give an oil which was triturated with ethyl acetate to give 1H-3-(4-fluorobenzyl)-4-(phenylsulfonyl)-7-cyano-2,3,4,5-tetrahydro-1,4-benzodiazepine, 4.5 g, 83%.

EXAMPLE 2

1H-3-Benzyl-4-(2-thienylsulfonyl)-7-cyano-2,3,4,5-tetrahydro-1,4-benzodiazepine

To a stirred solution of 3-benzyl-7-cyano-2,3,4,5-tetrahydro-1,4-benzodiazepine (34.5 g) in anhydrous methylene chloride (500 mL) and diisopropylethylamine (45 mL) was added a solution of 2-thienylsulfonyl chloride (34 g) in methylene chloride (200 mL) at 0° C. over 30 minutes. The mixture was stirred at room temperature for 40 hours. The solvent was removed to give an oil which was crystallized from ethanol (100 mL) to give 1H-3-benzyl-4-(2-thienylsulfonyl)-7-cyano-2,3,4,5-tetrahydro-1,4-benzodiazepine, 41 g, 76%.

EXAMPLE 3

1-(lmidazole-4-yl)methyl)-3-(4-fluorobenzyl)-4-phenylsulfonyl-7-cyano-2,3,4,5-tetrahydro-1,4-benzodiazepine To a stirred solution of 1H-3-(4-fluorobenzyl-4-(phenylsulfonyl)-7-cyano-2,3,4,5-tetrahydro-1,4-benzodiazepine (3.6 g) and imidazole-4-carboxaldehyde (1.7 g) in anhydrous methylene chloride (40 mL) was added trifluoroacetic acid (30 mL). The mixture was stirred at room temperature for 30 minutes and hydrotriethylsilane (2.76 mL) was added. The reaction mixture was stirred at room temperature for 5 hours. The solvent was removed and the residue was dissolved in methylene chloride (100 mL) and stirred with saturated sodium bicarbonate. The phases were separated. The organic layer was washed with 2N sodium hydroxide (2×50 mL). After drying, the solvent was removed to give a solid which was recrystallized from methanol (10 mL) to give 1-(imidazole-4-yl)methyl)-3-(4-fluorobenzyl)-4-(phenylsulfonyl)-7-cyano-2,3,4,5-tetrahydro-1,4-benzodiazepine, 4.00 g, 93%, MS, 502 (M+H).

EXAMPLE 4

1-(Imidazole-4-yl)methyl)-3-benzyl-4-(2-thienylsulfonyl)-7-cyano-2,3,4,5-tetrahydro-1,4-benzodiazepine hydrochloride To a stirred solution of 1H-3-benzyl-4-(2-thienylsulfonyl)-7-cyano-2,3,4,5-tetrahydro-1,4-benzodiazepine (31.7 g) and imidazole4-carboxaldehyde (20.1 g) in anhydrous methylene chloride (350 mL) was added trifluoroacetic acid (200 mL). The mixture was stirred at room temperature for 40 minutes. Hydrotriethylsilane (25 mL) was added to the reaction mixture over 15 minutes. After addition, the reaction mixture was stirred at room temperature overnight. The solvent was removed under vacuo. The residue was dissolved with methylene chloride (400 mL) and stirred with saturated sodium bicarbonate (100 mL) for 1 hour. The phases were separated. The organic layer was washed with 10% sodium hydroxide (3×100 mL) and saturated brine (150 mL) and dried. The solvent was removed to give a solid which was dissolved in ethyl acetate (200 mL). HCl in ether (1N, 150 mL) was added. The resulted slurry was filtered. The cake was washed with ethyl acetate and ether and dried to give 1-(imidazole4-yl)methyl)-3-benzyl-4-(2-thienylsulfonyl)-7-cyano-2,3,4,5-tetrahydro-1,4-benzodiazepine hydrochloride, 40.87 g, 95%, MS, 490 (M+H).

We claim:

1. A process for preparing a tertiary amine which comprises reacting a secondary amine with an aldehyde compound in the presence of a hydrotrialkylsilane and an acid selected from the group consisting of trifluoroacetic acid, trifluoromethanesulfonic acid and boron trifluoride.

2. The process of claim 1, wherein the secondary amine is a 4-substituted-2,3,4,5-tetrahydro-1,4-benzodiazepine.

3. The process of claim 1, wherein the aldehyde compound is imidazole-4-carboxaldehyde.

4. The process of claim 1, wherein the hydrosilane is hydrotrialkylsilane.

5. The process of claim 1, wherein the acid is trifluoroacetic acid.

6. A process for preparing a 1-alkyl-2,3,4,5-tetrahydro-1,4-benzodiazepine which comprises reacting a 4-substituted-2,3,4,5-tetrahydro-1,4-benzodiazepine with an aldehyde in the presence of a hydrotrialkylsilane and an acid selected from the group consisting of trifluoroacetic acid, trifluoromethanesulfonic acid and boron trifluoride.

7. The process of claim 6, wherein the 4-substituted-2,3,4,5-tetrahydro-1,4-benzodiazepine is 3-benzyl-4-(2-thienylsulfonyl)-7-cyano-2,3,4,5-tetrahydro-1,4-benzodiazepine.

8. The process of claim 6, wherein the aldehyde is imidazole-4-carboxaldehyde.

9. The process of claim 6, wherein the hydrosilane is hydrotrialkylsilane.

10. The process of claim 6, wherein the acid is trifluoroacetic acid.

11. A process for preparing a 1-alkyl-2,3,4,5-tetrahydro-1,4-benzodiazepine which comprises reacting a 4-substituted-2,3,4,5-tetrahydro-1,4-benzodiazepine with imidazole-4-carboxaldehyde in the presence of hydrotriethylsilane and trifluoroacetic acid.

12. A process for preparing 1-(imidazole-4-yl)methyl)-3-benzyl-4-(2-thienylsulfonyl)-7-cyano-2,3,4,5-tetrahydro-1,4-benzodiazepine which comprises reacting 1H-3-benzyl-4-(2-thienylsulfonyl)-7-cyano-2,3,4,5-tetrahydro-1,4-benzodiazepine with imidazole-4-carboxaldehyde in the presence of hydrotriethylsilane and trifluoroacetic acid.

* * * * *